United States Patent [19]
Amtower

[11] Patent Number: 5,362,444
[45] Date of Patent: Nov. 8, 1994

[54] METHOD FOR DISINFECTING A CONTACT LENS AND DETECTING THE PRESENCE OF AN OXIDATIVE DISINFECTANT

[75] Inventor: Patricia C. Amtower, Dana Point, Calif.

[73] Assignee: Allergan, Inc., Irvine, Calif.

[21] Appl. No.: 796,902

[22] Filed: Nov. 22, 1991

Related U.S. Application Data

[63] Continuation of Ser. No. 588,085, Sep. 25, 1990, abandoned.

[51] Int. Cl.$^5$ .............................................. A61L 2/16
[52] U.S. Cl. ...................................... 422/30; 422/28; 514/840
[58] Field of Search ................... 422/28, 30; 252/106; 424/616; 514/839, 840

[56] References Cited

U.S. PATENT DOCUMENTS

| | | | |
|---|---|---|---|
| Re. 32,672 | 5/1988 | Huth et al. | 252/95 |
| 3,183,173 | 5/1965 | Oakes | 435/10 |
| 3,694,384 | 9/1972 | Factor et al. | 521/25 |
| 3,910,296 | 10/1975 | Karageozian et al. | 134/2 |
| 4,283,491 | 8/1981 | Dappen | 435/10 |
| 4,295,851 | 10/1981 | Neumann et al. | 8/524 |
| 4,521,375 | 6/1985 | Houlsby | 422/29 |
| 4,568,517 | 2/1986 | Kaspar et al. | 422/30 |
| 4,670,178 | 6/1987 | Huth et al. | 252/95 |
| 4,851,353 | 6/1989 | Miike et al. | 436/71 |
| 4,863,627 | 9/1989 | Davies et al. | 422/28 |

FOREIGN PATENT DOCUMENTS

WO8605695  10/1986  WIPO .

OTHER PUBLICATIONS

The Encyclopedia of Chemistry, Third Edition, "Porphrins", Pp. 910–912, Hampel et al.
The Encyclopedia of Chemistry, Third Edition, "Phthalocyanine Compounds", Pp. 852–854, Hampel et al.
The Enzymes, vol. XII, Oxidation–Reduction, Part B, Electron Transfer (II) Oxygenases, Oxidases (I), Third Edition, Pp. 557–567, Paul D. Boyer.
Sheu et al, "Iron-Hydroperoxide-Induced Phenylselenization of Hydrocarbons (Fenton Chemistry)", American Chemical Society 1989.
Alexandratos et al, "Dual Mechanism Bifunctional Polymers: Polystyrene-Based Ion-Exchange/Redox Resins", American Chemical Society 1986.
Mazur et al, "Integration of Fundamental Polymer Science and Technology".
Sheu et al, "Iron-Induced Activation of Hydrogen Peroxide for the Direct Ketonization of Methylenic Carbon [C–$C_6H_{12}$ c–$C_6H_{10}$(O)] and the Dioxygenation of Acetylenes and Arylolefins", American Chemical Society 1990.
Alexandratos et al, "Synthesis and Characterization of Bifunctional Ion-Exchange/Coordination Resins", Macromolecules 1987, 20, 1191–1196.

Primary Examiner—Robert J. Warden
Assistant Examiner—Theresa A. Trembley
Attorney, Agent, or Firm—Frank J. Uxa

[57] ABSTRACT

An apparatus and method useful for disinfecting a contact lens are disclosed. The apparatus includes a color indicator element comprising a redox polymer containing a repeating unit which has a stable oxidized state and a stable reduced state. This color indicator element provides a color indication of the presence of the oxidative disinfectant, e.g., hydrogen peroxide, in the liquid medium.

8 Claims, 1 Drawing Sheet

METHOD FOR DISINFECTING A CONTACT LENS AND DETECTING THE PRESENCE OF AN OXIDATIVE DISINFECTANT

This application is a continuation of application Ser. No. 588,085, filed Sep. 25, 1990, now abandoned.

BACKGROUND OF THE INVENTION

The present invention relates to an apparatus and method useful for disinfecting a contact lens. More particularly, this invention relates to such an apparatus and method in which the presence of, and preferably the substantial absence of, an oxidative disinfectant is indicated.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are oxidative disinfectant, in particular hydrogen peroxide, disinfection systems. Disinfecting hydrogen peroxide solutions are effective to kill the bacteria and fungi which may contaminate contact lenses. However, residual hydrogen peroxide on a disinfected contact lens may cause irritation, burning or other trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

In order to avoid trauma to the eye caused by the presence of oxidative disinfectant on or in the lens, it would be advantageous to have an indication of the presence of such oxidative disinfectant. Additionally, it would be advantageous to have an indication of the substantial absence of such oxidative disinfectant, e.g., so that one would know it was safe to place the disinfected lens into one's eye.

There continues to be a need for a contact lens care system which effectively disinfects a contact lens and provides an indication of the presence of the oxidative disinfectant so that the disinfected lens can be safely and comfortably worn.

SUMMARY OF THE INVENTION

A new apparatus and method for disinfecting, and preferably cleaning, contact lenses has been discovered. The present system provides a clear and positive indication of the presence of an oxidative disinfectant, in particular hydrogen peroxide, in the lens disinfecting medium. This indication warns the lens wearer not to place the lens directly from the oxidative disinfectant-containing medium into the eye. Importantly, the means by which this indication is given is safe, preferably is useful when peroxidases, such as catalase, alone are used to destroy residual oxidative disinfectant, does not interfere with the disinfecting method and has no substantial detrimental effect on the lens being disinfected. In addition, the present indicator preferably can be used many times, thus providing a cost effective approach to increasing the safety of contact lens disinfection.

In one broad aspect, the present invention is directed to an apparatus useful for disinfecting a contact lens which comprises a cup means and a color indicator means. The cup means acts to hold a liquid medium containing an oxidative contact lens disinfectant, in particular hydrogen peroxide. The color indicator means is adapted to be located at least partially in this liquid medium in the cup, and acts to provide a color indication of the presence of the oxidative contact lens disinfectant in the liquid medium. The color indicator means comprises a redox polymer containing a repeating unit which has a stable oxidized state and a stable reduced state.

In another broad aspect of the present invention, a method for disinfecting a contact lens is provided. This method comprises contacting a contact lens to be disinfected with a liquid medium containing an oxidative disinfectant, in particular hydrogen peroxide, at conditions to effectively disinfect the contact lens. This contacting occurs in the presence of a redox polymer, as described herein, in an amount effective to provide a color indication of the presence of the oxidative disinfectant in the liquid medium.

DETAILED DESCRIPTION OF THE INVENTION

The present invention is of value where oxidative disinfectants, in particular hydrogen peroxide, are used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by such oxidative disinfectants.

Although any oxidative disinfectant which is able to effectively disinfect a contact lens and oxidize the redox polymer may be used, the much preferred oxidative disinfectant is hydrogen peroxide, especially aqueous solutions including hydrogen peroxide.

The present lens disinfecting apparatus includes a cup means, preferably a substantially transparent cup means, and a color indicator means.

The cup means acts to hold a liquid medium containing an oxidative contact lens disinfectant. Such cup means may be made of any suitable material, such as, for example, glass, polymeric materials and the like, which are resistant to the action of the oxidative disinfectant and have no substantial detrimental effect on the lens being disinfected. Examples of useful materials of construction include polymethylmethacrylate, polysulfone, acrylonitrile-butadiene-styrene terpolymers, polyphenylene oxide and the like. Preferably, the cup means, or at least a portion thereof, is substantially transparent so that the color indication or indications of the present system can be easily visually monitored.

The present color indicator means is adapted to be located at least partially in the liquid medium in the cup means. The color indicator means acts to provide a color indication of the presence of the oxidative contact lens disinfectant in the liquid medium, and preferably a different color indication of the substantial absence of the oxidative disinfectant in the liquid medium, more preferably while the contact lens is in the liquid medium. The color indicator means comprises a redox polymer containing a repeating unit which has a stable oxidized state and a stable reduced state. Such redox polymer may be soluble or substantially insoluble in the liquid medium in which it is used. In one useful embodiment, the redox polymer itself has substantial solubility in the liquid medium, but is associated with, e.g., bonded to, adhered to or otherwise attached to, a matrix material, e.g., a cation exchange resin, which is substantially insoluble in the liquid medium to form a color indicator composite which is substantially insoluble in the liquid medium. In any event, such redox polymers are preferably substantially unable to penetrate or otherwise substantially interfere with the lens being treated.

The redox polymers useful in the present invention may be selected from those which are capable of functioning as described herein. As used herein, the term "redox polymer" refers to a material having a plurality of repeating units each of which repeating units include one or more locations capable of being oxidized and/or reduced, preferably both oxidized and reduced reversibly. The redox polymers are preferably derived directly from polymerization processing, rather than, for example, from ion exchange or other ion addition or complexing, or post-polymerization processing. Put another way, the redox characteristic of the presently useful redox polymers is preferably an inherent property of the polymer, rather than a feature added after the polymer is formed. The present redox polymers may be substantially metal-free, although certain metals, in particular transition metals, may be included, e.g., by impregnation, ion exchange, complexing and/or other techniques, to provide one or more useful properties to the polymer. For example, metal-containing ions may be associated with the presently useful redox polymers to facilitate providing a clear color indication of the presence and/or substantial absence of the oxidative disinfectant by the metal-containing ions themselves changing oxidation states and colors. Care should be exercised in using such metal-containing ions to avoid having such ions become disassociated from the redox polymer, and possibly contaminate the lens being treated.

In one embodiment, the repeating units of the presently useful redox polymer are cationic in the oxidized state. The redox polymer is preferably oxidizable, i.e., the repeating units of the redox polymer are oxidizable to the oxidized state, by the oxidative disinfectant in the liquid medium.

Although any suitable redox polymer may be employed, preferred are polymers which have a repeating unit in the oxidized state which contains the bipyridinium unit, that is

I

More preferably, the bipyridinium unit included has the following structural formula

II

Such repeating unit preferably further includes a xylylene group. Such polymers may be soluble or insoluble and are more fully described in Factor, et al U.S. Patent 3,694,384 which is incorporated in its entirety by reference herein.

These polymers are readily prepared by reacting a xylylene halide, generally xylylene chloride or xylylene bromine with bipyridyl. The xylylene halide can be any of the three isomers; ortho-, meta- or para-xylylene dihalide.

The reaction between the xylylene dihalide and the bipyridyl proceeds at room temperature. The reaction is conveniently carried out in a solvent for the reactants which is a non-solvent for the polymer. The particular solvent used is not critical and a convenient solvent is acetonitrile. Other solvents can of course be used. Acetonitrile is a very good solvent for the reactants and the polymer precipitates permitting recovery by filtration of the reaction mixture. Since no other product is produced, the filtrate can be used as the solvent in a succeeding reaction without purification. The polymer so produced is a polysalt in which the anions are the halide anion corresponding to the halide of the xylylene dihalide used in preparation of the polymer and the cation is the bipyridinium dication, e.g., shown above.

These polymers, as produced, are in the oxidized form and are readily soluble in water and various aqueous media forming colorless solutions, although in the solid state, they are yellow. When a reducing agent such as sodium dithionite, zinc dust, etc., is added to an aqueous solution containing such polymers, a deep blue to blue-violet color is produced depending on the concentration of the polymer. In the reduced cationic form, the polymer has repeating units having the formula:

III-A

III-B

Because this unit is a delocalized free radical, it is recognized that it is a resonant structure which is conveniently illustrated by Formulas III A and III B. With strong reducing agents, for example, sodium metal, complete reduction to a neutral, red polymer with repeating units having the formula:

IV can occur.

The aqueous solution containing the reduced polymer, either having Formula III or IV when shaken in the presence of air rapidly decolorizes as the polymer oxidizes back to the form having units of When a polymer is desired which is not water-soluble, two techniques can be used. One technique is to replace some or all of the xylylene dihalide with a tris(-halo-methyl) benzene, for example, mesityl trihalide. This produces cross-linking due to the trifunctionality of the trihalo compound. The other technique is to use an entirely different method of preparing the polymer which entails reaction of a xylylene dihalide with 4-cyanopyridine to form the bis-4-cyanopyridinium salt of xylylene dihalide. This salt is reduced with a reducing agent, such as sodium dithionite, to produce a polymer with repeating units such as in Formulas III A and III B. A side reaction occurs which produces a polymer which is not water-soluble apparently due to some cross-linking.

Other redox polymers which may be utilized include vinyl substituted pyridine polymers with ruthenium, vinylferrocene polymers, vinylpiridinium polymers, polymers derived from vinylpiridinium derivatives, and the like and mixtures thereof.

In the event the redox polymer itself has substantial solubility in the liquid medium, it is preferred to associate such substantially soluble redox polymer with a matrix material which is substantially insoluble in the liquid medium so that the redox polymer is maintained in a separate phase relative to the liquid medium. This is particularly useful when both the oxidized and reduced states of the redox polymer are charged species, especially when both states are either cationic or anionic. For example, the above-described polymers including the bipyridinium unit are cationic both in the oxidized and reduced states. The soluble cationic polymers, such as the polymers including the bipyridinium unit, can be bonded to conventional, water insoluble cation exchange resins, e.g., using conventional ion exchange techniques. Such water insoluble cation exchange resins nave the ability to exchange the cationic redox polymer for the cation on the resin and to maintain such cationic redox polymer bonded to the resin during the contact lens disinfecting processing. Any suitable cation exchange resin may be employed provided it functions as described herein and has no substantial detrimental effect on the lens disinfecting process or on the lens being disinfected. Among the useful cation exchange resins are substantially water insoluble organic polymeric materials which include anionic groups, in particular acidic groups, preferably acidic groups selected from sulfonic acid groups, phosphonic acid groups, phosphinic acid groups, carboxylic acid groups and the like and mixtures thereof.

Specific examples of cation exchange resins useful in the present invention include cross-linked polystyrene, cross-linked styrene-divinylbenzene copolymers, insoluble perfluoro polymers (such as those sold by E. I. dupont de Nemours & Co. under the trademark Nafion), cross-linked polysacchrides, cross-linked polyamides, cross-linked polyethylene, cross-linked polyacrylic acid, and the like and mixtures thereof. Of course, such resins are appropriately substituted or otherwise modified, e.g., with acidic groups as noted above, so as to be effective cation exchangers. The insoluble redox polymers and the insoluble matrix materials carrying redox polymers preferably have sufficient porosity or permeability to allow adequate intimate contact between the liquid medium, in particular the oxidative disinfectant in the liquid medium, and the redox polymer, e.g., located in the interior, away from the external surface, of the color indicator means so that the color indication or indications to be provided by the color indicator means are visually observable.

The color indicator means, in use, is located in the liquid medium employed to disinfect a contact lens. Thus, the color indicator means can be secured in the inside, i.e., the interior space of the cup means where the liquid medium is held, of the cup means, may be adapted to move freely within the liquid medium in the cup means, or may be an integral part of the cup means.

For example, in the event, the color indication means is secured in the inside of the cup means, it can comprise a band or other piece of material adhesively or otherwise secured to the cup means. The color indicator means may be separate and apart from the cup means, such as in the form of a single disc or tablet, or a plurality of particles. In one embodiment, when the color indicator means is in the form of small particles, a retainer means, e.g., a screen element or ion permeable membrane, can be provided in the cup means to keep the particles in place, and at the same time, allow the liquid medium in the cup means to freely contact the particles.

The color indicator means may be integral with the cup means. That is, for example, the cup means can be made at least in part from the material used as the color indicator means. In one particularly useful embodiment, the material used to make the cup means and the redox polymer, of the color indicator means are physically mixed together and processed, e.g., molded, to form the cup means.

The present apparatus preferably further includes a basket means acting to hold a contact lens in the liquid medium in the cup means. The color indicator means can be secured to the basket means or can be an integral part of the basket means. The basket means can be made of the same or different material or materials relative to the material or materials used to make the cup means. Preferably, the lens means is substantially opaque, rather than transparent.

The cup means may have a removable cover, which may be made of the same or different material or materials used to make the cup means and which need not be transparent.

The liquid medium used in disinfecting a contact lens in the present, invention preferably includes a disinfecting amount of oxidative disinfectant, in particular hydrogen peroxide. Preferably, a disinfecting amount of oxidative disinfectant means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Aqueous hydrogen peroxide solutions, preferably containing about 0.2% or about 0.5% to about 6% of hydrogen peroxide (w/v), are known to be effective disinfecting solutions for contact lenses. These solutions are effective at killing bacteria and fungi which may be found on contact lenses. Typically, the amount of hydrogen peroxide used in the liquid medium is well in excess of that required to effectively disinfect a contact lens. Substantial excess hydrogen peroxide is used so that the lens disinfection can be completed in a reasonable period to time.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution. During the disinfecting contacting, it is preferred that the liquid aqueous medium have a pH in the range of about 3 to about 9, more preferably about 6 to about 8. The liquid medium, e.g., aqueous liquid medium, preferably includes a buffer which is present in an amount effective to maintain the pH of the liquid medium in the desired range. This buffer may be present in the liquid medium and/or may be introduced into the liquid medium. Among the suitable buffers or buffering agents which may be employed are those which are conventionally used in contact lens care products. Examples of useful buffers include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, an oxidative disinfectant destroying component, hereinafter referred to as an ODDC, is included in a solid composition, e.g., a tablet, capsule, one or more solid particles and the like, which is preferably introduced into the liquid medium about the same time as the lens to be disinfected is introduced into the liquid medium. Such solid compositions include one or more ODDCs in an amount effective to destroy all the residual oxidative disinfectant remaining in the liquid medium after the lens has been disinfected and preferably reduce the redox polymer of the color indicator system to the reduced state. In certain instances, the redox polymer of the color indicator means may act to promote the destruction of the oxidative disinfectant in the liquid medium.

Thus, such preferred solid compositions, which are preferably initially contacted with the oxidative disinfectant-containing liquid medium at substantially the same time as is the lens to be disinfected, allow for effective lens disinfection and, in addition, effectively destroy the residual oxidative disinfectant remaining in the oxidative disinfectant-containing liquid medium so that the disinfected lens can be removed from the liquid medium and placed directly into the eye for safe and comfortable wear. If, as is preferred, such compositions also reduce the redox polymer of the color indicator means to the reduced state, a second color indication of the substantial absence of the oxidative disinfectant is provided while the contact lens remains in the liquid medium, thus giving added assurance to the lens wearer that it is safe to remove the lens from the liquid medium and wear the disinfected lens. Such preferred compositions may be present in the form of at least one item, e.g., tablet, capsule, one or more solid particles and the like, which includes a coated portion, e.g., a core such as a core tablet, and a barrier component. The coated portion includes the ODDC or ODDCs. The barrier component acts to delay the release of the ODDC or ODDCs from the coated portion into the liquid medium for a period of time, preferably sufficient to allow the lens to be disinfected. Preferably, the barrier coating substantially surrounds the coated portion.

Any suitable ODDC may be employed provided such ODDC has no substantial detrimental effect on the present system, on the disinfected lens or on the wearer of the disinfected lens. Among the useful ODDC are oxidative disinfectant reducing agents, peroxidases (meaning to include therein catalase) and mixtures thereof. One important advantage of the present system is that when peroxidases are used to destroy the oxidative disinfectant, such peroxidases preferably also reduce the redox polymer, so that no other reducing agent need be included. In certain other redox systems, the peroxidases used are substantially ineffective in providing a reduced state redox material. The need to use a separate reducing agent is a major disadvantage of such other systems.

Examples of the oxidative disinfectant reducing agents which are useful in the present invention are alkali metal, in particular sodium, thiosulfates; thiourea; alkali metal, in particular sodium, sulfites; thioglycerol; alkali metal, in particular sodium, formiates; pyruvic acid and salts of pyruvic acid, N-acetylcysteine, enediol compounds, e.g., ascorbic acid compounds, reductive acid compounds, isoascorbic acid compounds, glyoxylic acid compounds, squaric acid compounds, dihydroxymaleic acid compounds, dihydroxyfumaric acid compounds and mixtures thereof. Typical examples of the foregoing ene-diol compounds are the acids themselves, e.g., ascorbic acid, ophthalmically acceptable salts of such acids, e.g., sodium ascorbate, ophthalmically acceptable esters of such acids, e.g., ascorbyl palmitate and any other ophthalmically acceptable derivatives of such acids, e.g., that retain the ene-diol molecular structure mixtures thereof and the like. A particularly useful peroxidase is catalase. The peroxidases, and especially catalase, are very beneficial in the present invention since such ODDCs are effective to substantially eliminate hydrogen peroxide from a liquid medium in a reasonable period of time, e.g., on the order of about 1 minute to about 12 hours, preferably about 5 minutes to about 1 hour, after the ODDC is initially released into the liquid medium.

The amount of ODDC employed is preferably sufficient to destroy all the oxidative disinfectant present in the liquid medium into which the ODDC is placed and preferably reduce the redox polymer to the reduced state. Excess ODDC may De employed. Very large excesses of ODDC are to be avoided since the ODDC itself may cause problems with the disinfected lens and/or the ability to safely and comfortably wear such disinfected lens. When catalase is employed a part of the ODDC, it is preferably present in an amount of about 100 to about 1000, more preferably about 150 to about 700 units of catalase activity per milliliter of liquid medium. For example, an especially useful amount of catalase for use in an aqueous solution containing about 3% (w/v) hydrogen peroxide is about 520 units of catalase activity/ml of solution.

The delayed release of the ODDC or ODDCs into the liquid medium may be accomplished in any one of many suitable ways, a number of which are conventional and well known in the art. For example, the barrier, component, e.g., coating, may be provided by coating a core tablet, or other particle, containing the ODDC or ODDCs with a slow dissolving coating material, which may ultimately be completely or only partially soluble in the liquid medium, or by including the ODDC or ODDCs in a matrix from which it may be slowly leached. Also, the matrix may be coated with a slow dissolving material so that the start of the slow release is delayed. The delayed release form of the ODDC or ODDCs is preferably such that substantially no release occurs during a delay period followed by rapid and substantially complete release of the ODDC or ODDCs at the end of the delay period. Such a result may be obtained by coating the ODDC or ODDCs with a slow dissolving coating.

Barrier components suitable as either coatings or as matrices, include water soluble vinyl polymers, such as polyvinylpyrrolidone, polyvinylalcohol and polyethyleneglycol; water soluble proteins; polysaccharide and cellulose derivatives, such as methyl cellulose, hydroxypropylmethyl cellulose, sodium carboxymethylcellulose; alginic acid and its salts and other derivatives; and the like and mixtures thereof. Mixtures of the above materials may be used.

The amount of barrier component used is not critical in the present invention provided that such barrier component functions as described herein. The barrier component or components may suitably be present in the range of about 1% to about 20% or more, based on the weight of the ODDC or ODDCs.

The solid compositions may be produced using any one of many suitable methods, a number of which are conventional and well known in the art.

The solid compositions may include other components, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Pat. No. RE 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen of the disinfectant to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species are *B. subtilis, B. licheniformis* and *B. pumilis.* Organisms in this sub-class produce little or no neutral protease or amylase. The subtilisin B sub-class is made up of enzymes from such organisms a *B. subtilis, B. sibtilis vat. amylosacchariticus, B. amyloliquefaciens* and *B. sibtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Solid compositions which include such lens cleaning enzymes may be structured to release the enzyme, into the liquid medium which contacts the composition, at any time relative to the other component or components of the composition provided that the released enzyme is effective at the conditions present in the liquid medium to perform the cleaning function, as described herein. In one particularly useful embodiment, the cleaning enzyme is released into the liquid medium substantially immediately upon introducing the solid composition into the liquid medium.

In the event that a debris removing enzyme is present, the contact lens in the liquid medium is effectively cleaned of such debris. This cleaning action can occur before the lens is disinfected, at the time the lens is being disinfected, or after the lens is disinfected.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to substantially completely disinfect the lens being treated. Such contacting times can be in the range of about 1 minute to about 12 hours or more.

After such contacting, the liquid medium preferably includes substantially no residual, oxidative disinfectant and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

DETAILED DESCRIPTION OF THE DRAWINGS

Figures 1, 2, 3, 4, 5:
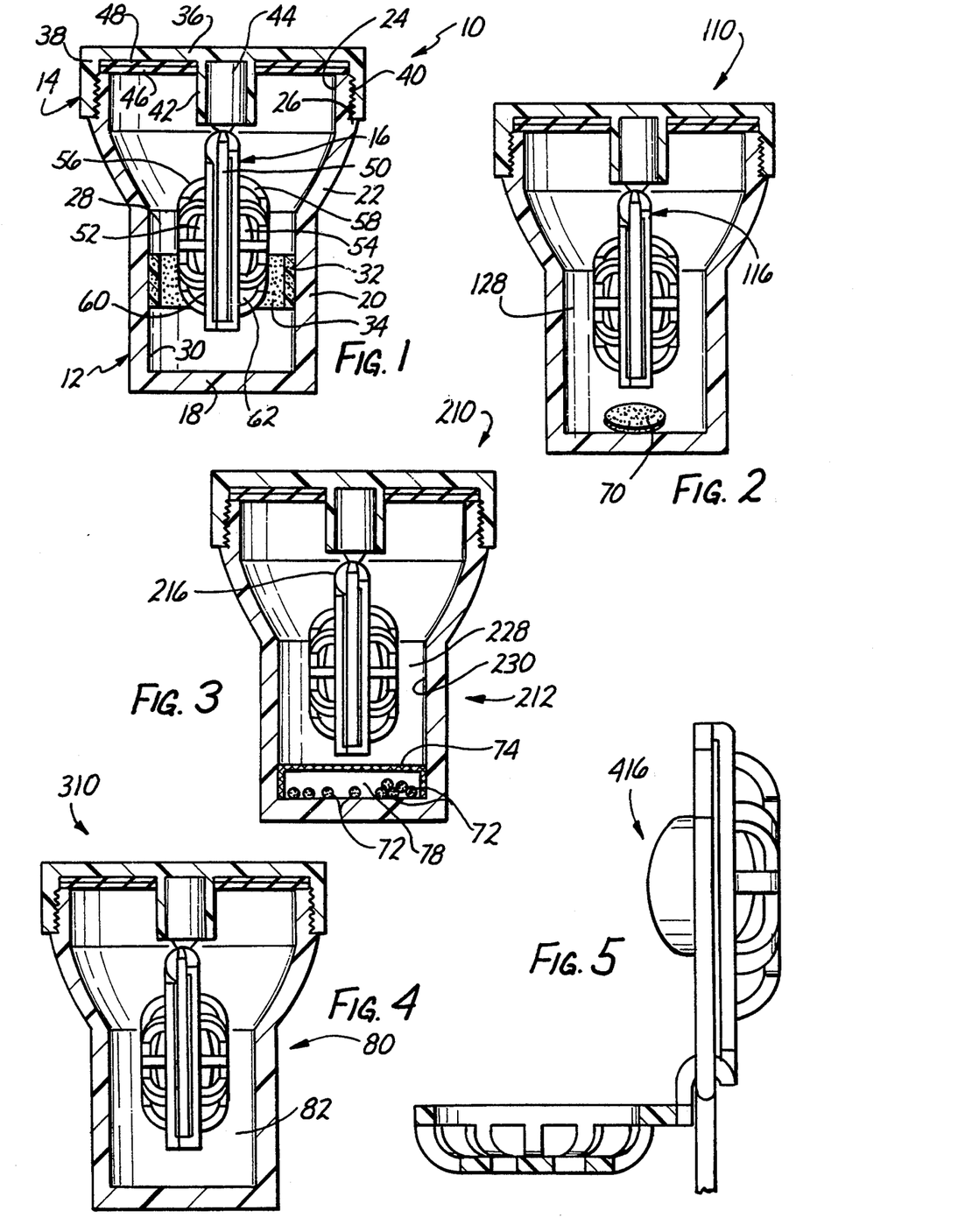
FIG. 1 is a front elevation view, partly in cross-section, illustrating one embodiment of the present apparatus.
FIG. 2 is a front elevation view, partly in cross-section, illustrating another embodiment of the present apparatus.
FIG. 3 is a front elevation view, partly in cross-section, illustrating an additional embodiment of the present apparatus.
FIG. 4 is a front elevation view, partly in cross-section, illustrating a further embodiment of the present apparatus.
FIG. 5 is a front elevation view, partly in cross-section, illustrating another embodiment of the lens basket of the present apparatus.

Referring now to FIG. 1, a lens disinfection apparatus, shown generally at 10, includes a lens container 12, a cover 14, and a lens basket 16.

Lens container 12 is made of a transparent, thermoplastic polymeric material, such as polymethylmethacrylate, and is made, e.g., molded using conventional techniques, as a single unit. Lens container 12 includes a bottom wall 18 and a sidewall 20. The upper portion 22 of sidewall 20 is flared outwardly. The top 24 of sidewall 20 includes a threaded outer surface 26. The cross-section of lens container 12 parallel to bottom wall 18 is generally circular. Lens container 12 defines an interior space 28 in which is placed a hydrogen peroxide-containing aqueous liquid medium.

Within interior space 28 and secured to the inner surface 30 of sidewall 20 is a color indicator band 32, which is made of a water-insoluble redox polymer containing xylylene-4,4'-bipyridinium units, which polymer is made in accordance with the procedure outlined in Example 3 of Factor et al U.S. Pat. No. 3,694,384. Alternately, color indicator band 32 can be derived from a water insoluble cation exchange resin, such as cross-linked sodium poly (styrene sulfonate), and a water-soluble redox polymer containing bipyridinium units as in Example 4 of Factor et al U.S. Pat. No. 3,694,384, e.g., using conventional ion exchange techniques. In any event, the entire color indicator band 32 is substantially insoluble in the liquid medium and is yellow in color in the presence of hydrogen peroxide.

The color indicator band 32 is generally right circular cylindrical in configuration and defines a through space 34 through which liquid can freely flow. Band 32 can be adhesively secured to inner surface 30 and is conveniently placed in interior space 28 to be completely submerged in the hydrogen peroxide-containing aqueous liquid medium during contact lens disinfecting.

Cover 14 includes a top wall 36 and a downwardly depending sidewall 38. Cover 14 is made of a non-transparent, thermoplastic polymeric material, such as polyphenylene oxide. Top wall 36 is generally circular and the cross-section of sidewall 38 parallel to top wall 36 is generally circular. Sidewall 38 includes a threaded inner surface 40 the threads of which matingly engage the threads of threaded outer surface 26 to secure cover 14 to lens container 12. Cover 14 also includes a central, circular hollow projection 42 which, extends downwardly into lens container 12 when cover 14 is secured to lens container 12. An attachment element 44 of lens basket 16 is secured, e.g., by adhesive, interference fitting and the like, in the hollow space defined by projection 42. In this manner, lens basket 16 is secured to cover 14. A pair of foamed polymeric sealing elements 46 and 48 are fitted on the underside of cover 14 around projection 42 and act to provide a substantially liquid tight seal when cover 14 is secured to lens container 12.

Lens basket 16 is made of a non-transparent, thermoplastic polymeric material, such as polyphenylene oxide. Like lens container 12 and cover 14, lens basket 16 can be made, e.g., molded, using conventional techniques. As noted above, lens basket 16 includes attachment element 44 which is secured to cover 14. Extending downwardly from attachment element 44 is basket body 50 which includes left lens mount 52 and right lens mount 54. Basket body 50 includes a series of through holes (not shown) which allow liquid to freely pass through the basket body.

A left basket cover 56 and a right basket cover 58 are both hingedly secured to basket body 50 and are structured to be "snapped" closed around left lens mount 52 and right lens mount 54, respectively, as desired, to form a left lens compartment 60 and a right lens compartment 62, respectively. The basket covers 56 and 58 are made separately from the other components of the lens basket 16. Each of the basket covers 56 and 58 include a series of through holes which allow liquid to flow freely through. However, these through holes are sized so that the contact lenses in lens compartments 60 and 62 cannot be removed when the lens covers 56 and 58 are closed. Left basket cover 56 may be marked with a "L" to indicate that it is to be used with the left contact lens. Similarly, the right basket cover 58 may be marked with a "R" to indicate that it is to be used with the right contact lens.

Lens disinfection apparatus 10 may be used as follows. With cover 14 removed from lens container 12, the contact lenses to be disinfected are placed on the appropriate left and right lens mounts 52 and 54, respectively and the left and right basket covers 56 and 58 are snapped closed.

A quantity, e.g., about 10 ml, of a 3% (w/v) hydrogen peroxide aqueous solution is placed in the interior space 28 of lens container 12 and completely immerses band 32. After the hydrogen peroxide solution is added, the band 32 is yellow in color, indicating the presence of hydrogen peroxide in the interior space 28. Cover 14 is applied to lens container 12 and secured in place. The contact lenses in lens compartments 60 and 62 are completely submerged in the hydrogen peroxide solution. Over a period of time, e.g., on the order of about 4 hours, the contact lenses are effectively disinfected. However, the band 32 remains yellow indicating the continued presence of hydrogen peroxide.

At this point, the cover 14 is removed from the lens container 12 and a tablet containing sufficient catalase to destroy the remaining hydrogen peroxide in the solution and to provide the redox polymer in the band 32 in a reduced state is added to the solution and the cover 14 is again secured to the lens container 12.

After another period of time, e.g., about one (1) hour, the band 32 is blue-violet in color, indicating that the solution in interior space 28 contains substantially no hydrogen peroxide. The contact lens can then be removed from the lens compartments 60 and 62, rinsed with saline solution, and placed directly into the wearer's eyes for safe and comfortable wear.

Several alternative approaches to disinfecting, and cleaning, contact lenses using apparatus 10 are possible. For example, the catalase with a delayed release coating can be added to the hydrogen peroxide-containing solution at substantially the same time the contact lenses are first contacted with this solution. The band 32 is yellow in color indicating the presence of hydrogen peroxide. After a period of time, the delayed release coating dissolves releasing the catalase into the solution. After another period of time, the band 32 is blue-violet in color indicating that the solution in interior space 28 includes substantially no hydrogen peroxide. The disinfected contact lenses can be rinsed with saline solution and placed in the wearer's eyes for safe and comfortable wear.

Another alternative involves coating the delayed release coating with a hydrogen peroxide active enzyme, e.g., subtilisin A enzyme, in an amount effective to remove at least one type of debris, e.g., proteinaceous debris. In this embodiment, the enzyme/catalase combination with the delayed release coating can be added to the hydrogen peroxide-containing solution at substantially the same time the contact lenses are first contacted with this solution. The band 32 is yellow in color indicating the presence of hydrogen peroxide. After a period to time, during which the hydrogen peroxide-active enzyme removes proteinaceous debris from the contact lenses and the contact lenses are effectively disinfected, the delayed release coating releases the catalase into the solution. After another period of time, the band 32 is blue-violet in color, indicating that the solution in interior space 28 includes substantially no hydrogen peroxide. The cleaned and disinfected contact lenses can be rinsed with saline solution to remove the subtilisin A enzyme and placed in the wearer's eyes for safe and comfortable wear.

FIG. 2 illustrates another embodiment of the present invention. Except as expressly stated elsewhere herein, this lens disinfection apparatus, shown generally at 110, is constructed and functions in a manner similar to lens disinfection apparatus 10. Components of apparatus 110 which correspond to components of apparatus 10 are indicated by corresponding reference numerals increased by 100.

One primary difference between apparatus 110 and apparatus 10 is that apparatus 110 does not include a color indicator band, such as color indicator band 32. Instead apparatus 110 includes a color indicator disc 70, which is made of the same material, as is color indicator band 32. That is, color indicator disc 70 is made of a water insoluble redox polymer or a composite of a water soluble redox polymer and a water insoluble cation exchange resin. Color indicator disc 70 is included in the interior space 128 of apparatus 110 during the time the contact lenses in lens basket 116 are being disinfected or cleaned and disinfected.

Color indicator disc 70 is yellow in color, indicating the presence of hydrogen peroxide, and is blue-violet in color, indicating the substantial absence of hydrogen peroxide.

FIG. 3 illustrates an additional embodiment of the present invention. Except as expressly stated elsewhere herein, this lens disinfection apparatus, shown generally at 210, is constructed and functions in a manner similar to lens disinfection apparatus 10. Components of apparatus 210 which correspond to components of apparatus 10 are indicated by corresponding reference numerals increased by 200.

One primary difference between apparatus 210 and apparatus 10 is that apparatus 210 does not include a color indicator band, such as color indicator band 32. Instead, apparatus 210 includes a plurality of color indicator beads 72 which are located at or near the bottom of interior space 228. A screen insert 74 is fitted within the inner wall 230 of lens container 212. Screen element 74 includes a plurality of holes sized so as to allow free access of the liquid material inside inner space 228 across screen element 74. At the same time, these holes are insufficiently large to allow the color indicator beads 72 to escape the compartment 78 defined by screen element 74 and the bottom portion of lens container 212.

Color indicator beads 72 are made of the same material as color indicator band 32. That is, color indicator beads 72 are made of a water insoluble redox polymer or a composite of a water soluble redox polymer and a water insoluble cation exchange resin. Color indicator beads 72 are included in the space 78 defined by screen element 74 and the bottom portion of lens container 212 during the time the contact lenses are being disinfected or cleaned and disinfected. Color indicator beads 72 are yellow in color, indicating the presence of hydrogen peroxide, and are blue-violet in color, indicating the substantial absence of hydrogen peroxide.

If desired, the screen element 74 can be removed from lens container 212 to replace color indicator beads 72. One important advantage of lens disinfection apparatus 210, for example relative to lens disinfection apparatus 110, is that the color indicator beads 72 remain in place between uses of apparatus 210 and are, therefore, not prone to being lost. The color indicator disc 70 of lens disinfection apparatus 110 can be removed between uses and become lost.

FIG. 4 illustrates a further embodiment of the present invention. Except as expressly stated elsewhere herein, the lens disinfection apparatus, shown generally at 310, is constructed and functions in a manner similar to lens disinfection apparatus 10. Components of apparatus 310 which correspond to components of apparatus 10 are indicated by corresponding reference numerals increased by 300.

One primary difference between apparatus 310 and apparatus 10 is that apparatus 310 does not include a color indicator band, such as color indicator band 32.

Instead, apparatus 310 is provided with a color indicating lens container 80 which is made of a physical mixture of polymethylmethacrylate and the redox polymer described previously with regard to apparatus 10. This physical mixture of polymers is combined and then used to fabricate lens container 80, which is substantially transparent. Sufficient redox polymer is included so that the lens container has a yellowish haze in the presence of hydrogen peroxide.

Lens container 80 includes an interior space 82 in which is placed a hydrogen peroxide-containing aqueous liquid medium.

Lens container 80 is configured substantially similarly to lens container 12. Lens container 80 has a yellowish haze, indicating the presence of hydrogen peroxide in the aqueous liquid medium in interior space 82, and is blue-violet in color, indicating the substantial absence of hydrogen peroxide in such aqueous liquid medium.

FIG. 5 illustrates another embodiment of the lens basket of the present invention. Except as expressly stated elsewhere herein, this lens basket, shown generally at 416, is constructed and functions in a manner similar to lens basket 16. Components of lens basket 416 which correspond to components of lens basket 16 are indicated by corresponding reference numerals increased by 400.

One primary difference between lens basket 416 and lens basket 16 is the material of construction used in lens basket 416. Thus, lens basket 416 is made of a physical mixture of polyphenylene oxide and the redox polymer described with regard to lens disinfection apparatus 10. Sufficient redox polymer included so that the entire lens basket 416 is yellow in color in the presence of hydrogen peroxide.

Lens basket 416 can be effectively utilized as both a lens basket and a color indicator for the presence of hydrogen peroxide. A particularly useful embodiment would involve replacing lens basket 116 with lens basket 416 in lens disinfection apparatus 110 and removing color indicator disc 70. In this embodiment, lens basket 416 is yellow in color indicating the presence of hydrogen peroxide, and is blue-violet in color, indicating the substantial absence of hydrogen peroxide.

The following non-limiting examples illustrate certain aspects of the present invention.

EXAMPLE 1

This example illustrates a lens cleaning/disinfecting embodiment of the present invention, with specific reference to FIG. 3.

About 1 g of beads 72 made of the water insoluble redox polymer produced in accordance with Example 3 of Factor et al U.S. Pat. No. 3,694,384 is placed in the bottom portion 78 of interior space 228.

A pair of protein-based debris laden contact lenses are placed in lens basket 216. 10 ml of a saline solution containing 3% (w/v) of $H_2O_2$ and 0.3% by weight of boric acid is added to the interior space 228, and the lens basket 216 is positioned so that the contact lenses are completely submerged in the solution in lens container 212. The pH of this solution is about 7.5. At this point the beads 72 are yellow in color.

A layered, delayed release tablet is dropped into the solution in lens container 212. The center core of the tablet includes 2.0 mg of crystalline catalase. The outer layer of the tablet includes 0.4 mg of subtilisin A enzyme. A delayed release layer between the inner layer and the outer layer is structured and designed to dissolve sufficiently in two hours after being exposed to the solution in the lens container 212 to release the catalase into the solution.

Upon being dropped into the solution, the outer layer of the tablet dissolves to release the subtilisin A into the solution. The enzyme in the outer layer begins to attack and remove the protein-based debris on the lenses. Substantially all of the protein-based debris is removed from the lenses. In addition, the contact lenses are effectively disinfected. Two hours after the layered tablet is first dropped into the solution, the catalase is released into the solution and destroys the residual hydrogen peroxide in the solution and reduces the redox polymer in the beads 72 to a reduced state. At this point, the beads 72 turn blue-violet in color. Upon seeing the blue-violet beads 72, the lens wearer removes the cleaned/disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

EXAMPLE 2

Example 1 is repeated except that the water insoluble redox polymer beads are replaced by beads made of a composite of water soluble redox polymer and cross-linked sodium poly (styrene sulfonate) as described in Example 4 of Factor et al U.S. Pat. No. 3,694,384.

As in Example 1, the beads are yellow in color in the presence of hydrogen peroxide and turn blue-violet in color when the residual hydrogen peroxide in the solution is destroyed and the redox polymer is reduced to a reduced state. Upon seeing the blue-violet beads, the lens wearer removes the cleaned/disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

EXAMPLE 3

Example 1 is repeated except that the inner layer of the tablet contains 3.0 mg of N-acetylcysteine and no catalase.

After the beads turn from yellow to blue-violet in color, the cleaned/disinfected contact lenses are removed from the solution, rinsed with physiological saline solution to remove the subtilisin A enzyme and placed in the wearer's eyes. It is found that the contact lenses are effectively disinfected and cleaned of protein-based debris. The lens wearer experiences no discomfort or eye irritation from wearing the disinfected and cleaned contact lenses.

EXAMPLE 4

Example 2 is repeated except that the inner layer of the tablet contains 3.0 mg of N-acetylcysteine and no catalase.

After the beads turn from yellow to blue-violet in color, the cleaned/disinfected contact lenses are removed from the solution, rinsed with physiological saline solution to remove the subtilisin A enzyme and placed in the wearer's eyes. It is found that the contact lenses are effectively disinfected and cleaned of protein-based debris. The lens wearer experiences no discomfort or eye irritation from wearing the disinfected and cleaned contact lenses.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
    contacting a contact lens to be disinfected with a liquid medium containing hydrogen peroxide disinfectant at conditions to effectively disinfect said contact lens, said contacting occurring in the presence of a redox polymer which is and remains insoluble in said liquid medium at the conditions of said contacting and which contains a repeating unit which has a stable oxidized state and a stable reduced state in an amount effective to provide a first color indication of the presence of hydrogen peroxide in said liquid medium, said redox polymer being present in a separate phase from said liquid medium; and
    contacting said liquid medium with catalase present in an amount effective to destroy all the hydrogen peroxide in said liquid medium and to provide said insoluble redox polymer in a reduced state, thereby providing a second color indication of the absence of hydrogen peroxide in said liquid medium.

2. The method of claim 1 wherein said repeating unit is cationic in the oxidized state.

3. The method of claim 1 wherein said repeating unit in the oxidized cationic state contains the bipyridinium unit 4. The method of claim 1 wherein said redox polymer is associated with a matrix material which is insoluble in said liquid medium.

5. The method of claim 1 wherein said redox polymer is associated with a cation exchange resin which is insoluble in said liquid medium.

6. The method of claim 1 wherein said contacting steps are repeated using the same redox polymer.

7. A method for disinfecting a contact lens comprising:
    contacting a contact lens to be disinfected with a liquid aqueous medium containing hydrogen peroxide at conditions to effectively disinfect said contact lens, said contacting occurring in the presence of a redox polymer containing a repeating unit which has a stable oxidized state and a stable reduced state, said repeating unit in the stable oxidized state being cationic and containing the bipyridinium unit and a xylylene group, said redox polymer being present in an amount to provide a first color indication of the presence of hydrogen peroxide in said aqueous liquid medium, said redox polymer being present in an oxidized state during said contacting and in a separate solid phase from said liquid aqueous medium throughout said contacting; and, thereafter,
    contacting said liquid aqueous medium with catalase present in an amount effective to destroy all the hydrogen peroxide in said liquid aqueous medium and to provide said separate solid phase redox polymer in a reduced state, thereby providing a second color indication of the absence of hydrogen peroxide in said liquid aqueous medium.

8. The method of claim 7 wherein said contacting steps are repeated using the same separate solid phase redox polymer.

UNITED STATES PATENT AND TRADEMARK OFFICE
CERTIFICATE OF CORRECTION

PATENT NO. : 5,362,444
DATED : November 8, 1994
INVENTOR(S) : Amtower

It is certified that error appears in the above-indentified patent and that said Letters Patent is hereby corrected as shown below:

Column 3, line 57-68, please delete the illustration and insert in place thereof the following:

Column 5, line 49, delete "nave" and insert in place thereof --have--.
Column 5, line 67, delete "dupont" and insert in place thereof --duPont--.
Column 6, line 58, delete "present," and insert in place thereof --present--.
Column 8, line 53, delete "De" and insert in place thereof --be--.

Signed and Sealed this

Twenty-eighth Day of May, 1996

Attest:

BRUCE LEHMAN

Attesting Officer    Commissioner of Patents and Trademarks